United States Patent [19]

Clifford

[11] Patent Number: 4,736,322

[45] Date of Patent: Apr. 5, 1988

[54] CARDIOLOGICAL SIMULATOR

[76] Inventor: Ralph D. Clifford, 4821 Tinasa Way, San Diego, Calif. 92124

[21] Appl. No.: 754,173

[22] Filed: Jul. 12, 1985

[51] Int. Cl.[4] ............................................. G06F 15/42
[52] U.S. Cl. ................................... 364/413; 364/417; 364/578; 364/801; 128/695
[58] Field of Search ............... 364/415, 417, 478, 602, 364/607, 718, 801–802, 413; 371/23; 128/668, 672, 695, 699, 702

[56] References Cited

U.S. PATENT DOCUMENTS

| | | | |
|---|---|---|---|
| 3,991,304 | 11/1976 | Hillsman | 364/415 X |
| 4,204,261 | 5/1980 | Ruszala et al. | 364/607 |
| 4,205,386 | 5/1980 | Ruszala et al. | 364/607 |
| 4,211,237 | 7/1980 | Nagel | 364/417 X |
| 4,216,462 | 8/1980 | McGrath et al. | 364/415 X |
| 4,301,512 | 11/1981 | Keith et al. | 364/801 |
| 4,352,163 | 9/1982 | Schultz, Jr. et al. | 364/801 |
| 4,417,306 | 11/1983 | Citron et al. | 364/415 |
| 4,457,310 | 7/1984 | Swyer et al. | 364/417 X |
| 4,616,659 | 10/1986 | Prezas et al. | 364/417 X |

Primary Examiner—Gary V. Harkcom
Attorney, Agent, or Firm—Thomas J. Tighe

[57] ABSTRACT

A device and method for simulating the heartbeat, pressure, and respiration waveforms of a human being. A memory contains a plurality of sets of individual digitized samples of unique hearbeat rhythms. Another memory means contains a set of individual digitized samples of increments for generating a pressure waveform. A primary rhythm and a heartbeat rate are selected by an operator via a key pad. Optionally, a secondary rhythm and a number associated with that secondary rhythm is selected via the key pad. Also, a respirator rate and systolic and diastolic levels of blood pressure can be selected via the key pad. The selections can be stored in a user memory for future recall or they can be used for the immediate production of waveforms. The key pad communicates with a processor, preferably a microprocessor. The processor has program memory and data memory. The processor also has a plurality of bidirectional input-output ports. A first digital-to-analog converter communicates with one of the ports and outputs a signal simulating a heartbeat. A second digital-to-analog converter communicates with a second port and outputs a blood pressure waveform. A variable impedance circuit is the output for the respiration signal.

14 Claims, 2 Drawing Sheets

CARDIOLOGICAL SIMULATOR

BACKGROUND OF THE INVENTION

This invention relates to devices which create and transmit biological waveforms. More particularly, it relates to such devices that produce simulated electrocardiogram and blood pressure wave-forms.

An electrocardiograph is an instrument used to diagnose disorders of the heart. It detects and records the electrical impulse developed by the heart with each beat. A recording of the impulse is called an electrocardiogram, often abbreviated EKG.

To make a recording, electrical impulses from the heart are gathered from a plurality of points. Most commonly, electrodes, which are attached to wires from the electrocardiograph, are placed on a patient's right arm (RA), left arm (LA) and right leg (RL), the right arm or left arm electrodes being commonly used in conjuction with the RL electrode to sense the patient's respiration rate.

Impulses from a normal heart make records of a specific size and shape. In certain abnormal conditions, the recording shows changes in this pattern. A normal heart produces an impulse (herein, also called a rhythm) which is periodically and uniformly repeated, but an abnormal heartbeat will produce rhythms which are both normal and abnormal. The abnormal rhythms are known as arrhythmyias. Arrhythmias can be continuous or occur in combination with other rhythms.

These combined arrhythymias can be divided into four groups: (1) bigem, (2) trigem, (3) v/min, and (4) run/v. "Bigem" is short for "bigemini" which describes an impulse pattern comprised of one normal rhythm (herein, also called a primary rhythm) followed by an abnormal rhythm (herein, also called a secondary rhythm), the pattern being periodically repeated. "Trigem" is short for "trigemini" which describes an impulse pattern comprised of two normal rhythms followed by an abnormal rhythm, the pattern being periodically repeated. "V/min" is short for "ventrical premature beats per minute" which generally describes an impulse pattern comprised of uniformly repeating rhythms, but with some of the primary rhythms replaced by secondary rhythms, the secondary rhythms never occuring two or more in a row. "Run/v" is short for "run per ventrical premature beats" which generally describes an impulse pattern comprised of uniformly repeating primary rhythms, but with a primary rhythm being occasionally replaced by a run (one or more in a row) of secondary rhythms.

There exist devices which are used to monitor a patient's heartbeat, respiration, and blood pressure, and which are adapted to recognize normal and abnormal rhythms. They are commonly referred to as "computerized arrhythmyia systems." In many situations the life of a patient can depend on the ability of these systems to recognize dangerous arrhythmias and to sound an alarm in response thereto. Therefore the calibration and testing of these systems is very important.

This invention presents a means of testing and calibrating these systems. It simulates a patient in that this invention can be connected to an arrhythmyia system and produce impulses which simulate a wide variety of heartbeat patterns. This invention also produces signals which simulate the blood pressure and respiration patterns of a patient. It is capable of completely testing the recognition ability and responses of a conventional arrhthmyia system.

Other advantages and attributes of this invention will be readily discernible upon a reading of the text hereinafter.

SUMMARY OF THE INVENTION

This invention presents a device for simulating the physiology of a human, that is, certain significant biological waveforms. It comprises a central processing unit (CPU) adapted to be responsive to a control program, a program memory accessible for at least reading by the CPU and adapted to store a control program, a data memory accessible for reading and writing by the CPU, a plurality of data ports commonly referred to as input/output (I/O) ports adapted to provide a communication path between the CPU and devices external to the CPU, an input means responsive to input actions of an operator and adapted to communicate to the CPU, via a first I/O port, the inputs of the operator, a control program adapted to, in response to operator inputs, cause the CPU to output via a second I/O port, a periodic string of data groups, commonly referred to as bytes, each group representing an amplitude at some point in time of an electrocardiogram (EKG) waveform, and a digital to analog converter (DAC) adapted to convert the periodic string of data groups from the second I/O port to analog signals the amplitudes of which correspond to the amplitudes represented by the data groups.

An object of this invention is to provide a hand-held programmable device for simulating the EKG and blood pressure waveforms of a patient.

Other objects of this invention will be readily discernible upon a reading of the specification.

DESCRIPTION OF THE PREFERRED EMBODIMENT

Figure 1:
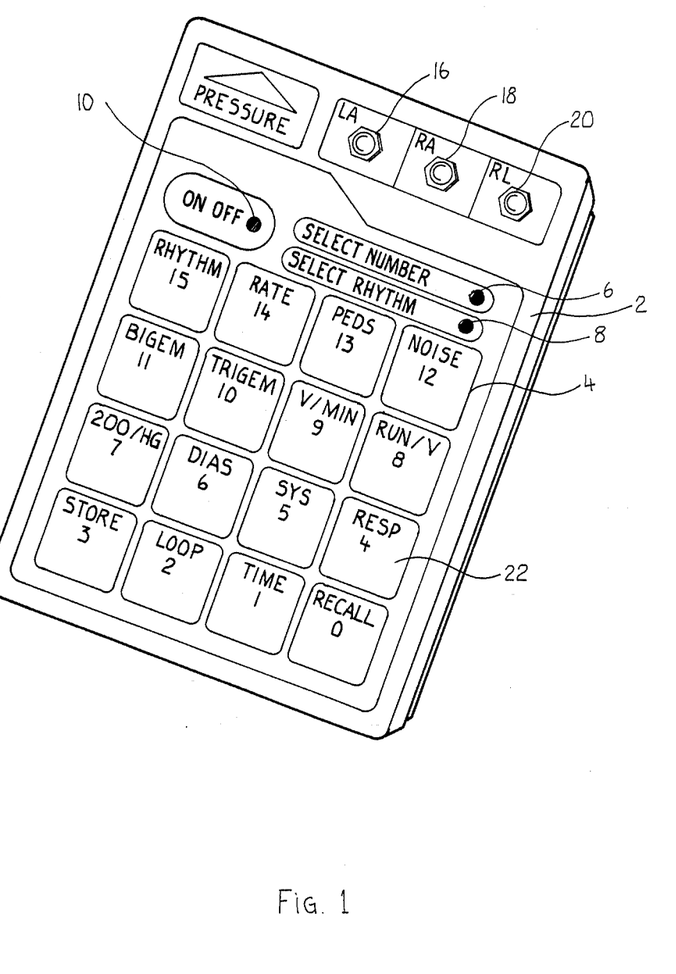
FIG. 1 is a pictorial representation of the entire device being hand-held.

Referring to FIG. 1, the device, generally designated 1, is shown as a hand-held device. It is comprised primarily of electronic circuits (not shown in this figure), a casing 2, a key pad 4, a plurality of indicators 6, 8, 10, e.g. light emitting diodes; and three electrical posts, 16, 18 and 20, labeled "LA", "RA", "RL", respectively. "LA", "RA" and "RL" correspond respectively to the left arm, right arm and right leg electrodes of conventional EKG and respiration monitors. Not shown is a fourth external electrical contact. The key pad comprises a matrix of 16 individual keys 22. Each key 22 hears indicia. Each indicium comprises a function label in English letters, a numeral, and a rhythm description. Regarding the numeric indicia, the keys are numbered progressively from 0 through 15.

The description will now focus on the keys re: (1) how they are used, and (2) how they relate to the functions of this device.

Each key 22 in the key pad 4 performs multiple functions. When selecting a rhythm, as hereinafter explained, an operator pushes the key that bears a description of the desired rhythm. For example, if the desired rhythm is atrial flutter then key 7 is pushed. When entering numbers, as hereinafter will be explained, an operator actuates the key or keys bearing the desired numerals. The key pad also serves as a function selecting means, as will be explained hereinafter. The light emitting diode (LED) indicators are used to inform the operator of the state of the device with regard to operator inputs.

As explained hereinafter, an operator can select both a primary rhythm and a secondary rhythm. The secondary rhythm is commonly referred to as an arrhythmyia. As used herein, the term "rhythm" generally refers to both primary and secondary rhythms. More particularly, the term "rhythm" refers to the EKG pattern created by a heart when it is not in a state of rest. For example, if the simulated heartbeat is of normal form with a rate of 80 beats per minute, then this invention will generate a normal sinus rhythm 80 times per minute, all rhythms being uniformly spaced apart in time. The term "waveform," when it refers to an EKG pattern, refers to the entire pattern.

In operation, an operator first selects a primary rhythm by actuating a "rhythm" key. A "select rhythm" LED 8 then lights to indicate to the operator that he or she is to select a desired primary rhythm. After actuating the key bearing a description of the desired rhythm, the operator then actuates a key labeled "rate." An LED 6 labeled "select number" then lights which indicates to the operator that he or she is to enter the rate of the primary rhythm, that is, the beats per minute. At this point the operator then enters a number representing the rate. Key entries for the primary rhythm and its rate are saved in device memory at locations labeled "Last Rhythm" and "Last Rate", respectively.

Once a primary rhythm has been entered, an operator has additional options. By actuating one of the four arrhythmia keys the operator is telling the device that he or she wishes to select a secondary rhythm, that is, an arrhythmyia. The secondary rhythm will occur in place of the primary rhythm at times based on a further operator input. A first arrhythmyia option is selected when the operator actuates the "v/min" key which then lights the "select rhythm" LED 8. The operator then actuates the key bearing a description of the secondary rhythm. Actuating the "rate" key again causes the "select number" LED 6 to light. The operator then enters a number corresponding to the number of secondary rhythms which will occur per minute. A control program in the device insures that the primary and secondary rhythms do not interfere with each other's completion and that there are never two secondary rhythms in a row. The device will automatically alter the timing relationship between the rhythms, depending on what physical condition the secondary rhythm represents.

A second arrhythmyia option permits the operator to select a secondary rhythm which will occur in multiples, that is, more than one in a row. This option is selected by actuating a "run/v" key. By actuating that key, the "select rhythm" LED 8 lights indicating to the operator that he is to select a rhythm. Once a rhythm is selected, the operator actuates the "rate" key. The "select number" LED 6 lights telling the operator that he or she is to select the number of times in a row that this second rhythm will occur. Once the number is entered, the device itself will insure that the two rhythms do not interfere with each other's completion. The occurrence of the secondary rhythms are controlled by the device to repeat every minute. Again, the control program evaluates the physiological significance between the two selected rhythms and automatically determines: (1) the delay between the primary rhythm's completion and the start of the secondary rhythm, and (2) the repetition rate of the secondary rhythm.

A third arrhythmyia option is selected by actuating a "bigem" key, after the primary rhythm and rate have been selected, followed by a selection of a secondary rhythm. Because this option simulates a bigeminal heartbeat condition, the device will ensure that a secondary rhythm occurs after each primary rhythm occurrence. There is no need for the operator to enter a rate for the secondary rhythm.

A fourth arrhythmyia option is selected by actuating a "trigem" key, after the primary rhythm and rate have been selected, followed by a selection of a secondary rhythm. Because this option simulates a trigeminal heartbeat condition, the device will ensure that a secondary rhythm occurs after each pair of primary rhythm occurrences.

Key entries for the secondary rhythm are saved in device memory at a location labeled "Last Arrhythmyia". In the cases of v/min and run/v arrhythmyias, the number entered with the secondary rhythm is saved in "Last Number of Arrhythmyias."

Continuing with the discussion of the operation as it relates to the keys, each rhythm can be modified to more realistically mimic real world conditions. One modifier is selected by actuation of a "peds" (pediatrics) key which causes the device to increase the high frequency components of the rhythm to more closely resemble that of an infant or small child. A second option is selected by actuation of a "noise" key. This option adds two common types of interference to the waveform, namely 60 Hz noise or baseline wander. Baseline wander is a variation, or wandering, of the dc level of a waveform caused by a patient's movement. These modifiers can be assigned to the waveform in any combination.

The device remembers which type of arrhytmyia (only one) has been selected and which modifiers have been selected by setting flags in a device memory location labeled "modifier flag byte." A flag is one bit of the memory location. Accordingly, the modifier flag byte has at least the following flags: bigem, trigem, v/min, run/v, peds, and noise.

Over and above the selection and creation of a waveform, the device is programmable. Once a waveform has been created, it can then be stored in a one of a plurality of user memory locations. All created attributes of the rhythm, including modifiers, options, and including respiration rate can be stored in a pseudo memory location. It is a pseudo memory location because there is not necessarily a one to one correspondence between a "user memory" location and a single memory location as defined by the electronic circuits.

There are a plurality of user memory locations to enable an operator to store a plurality of waveforms. Each waveform can have a run time value assigned to it. Preferrably the time value represents a time period from 1 to 150 minutes. This time value is automatically stored along with the other waveform data at a selected user memory location. The time value associated with a waveform is entered by actuating a "time" key and, thereafter, entering the time value by actuating keys bearing the appropriate numerical indicia. The time value is saved in device memory at a location labeled "Run Time."

A waveform is stored in the user memory location by actuation of a "store" key and then actuating a key bearing the appropriate numerical indicium for the user memory location. Preferably keys marked 0 through 11 are used by the control program to recognize and utilize 12 separate user memory locations. The keys designated 12 through 15 are reserved for fixed program sequences such as an automatic test sequence, as will be explained hereinafter. Each user memory location has the capacity to save at least all of the information contained in operational memory locations Last Rhythm, Last Rate, Last Arrhythmyia, Last Number Arrhythmyias, Modifier Flag Byte, and Run Time. These memory locations contain all the information necessary to reconstruct a stored EKG waveform and are all saved when the operator stores a waveform.

A waveform is recalled from its user memory location by actuation of a "recall" key and subsequent actuation of the key bearing the appropriate numerical indicium. The stored information is returned to the operational memory locations from which it was saved. It a waveform does not have a run time assigned to it, the device will continue to periodically generate the rhythms of the waveform until intervention by the operator or a suitable time-out occurs. Preferably, the device shuts off automatically after 4 hours.

If a waveform has a run time assigned to it, the device will cease generating that waveform after the time has expired and will retrieve a waveform from the next sequential user memory location. It will then create and transmit the new waveform.

Any user memory location can be designated a "loop" location by actuation of the "loop" key preceded by the designation of a user memory location as explained above. If in its progression through the user memory locations, the control program encounters a "loop" code, it will cause the device to jump back to the original recalled waveform. Thus, it provides the means for the device to run a continuous loop through one or more waveforms, each having a run time associated with it of greater than zero. If the device encounters a recalled waveform with a run time of zero, the device will shut itself off.

As explained before, automatic test sequences can be run by "recalling" them. An automatic test is selected by actuating the "recall" key and subsequently actuating a key reserved for such a test, preferably one of the keys numbered 12 through 15. The device follows the same procedure for recalling an automatic test as it does when recalling waveforms from user memory. The automatic tests are preprogrammed sequences of rhythms that are designed to stimulate conventional computerized arrhythmia monitoring systems. An arrhythmia monitoring system, if working properly, will produce a repeatable set of outputs, such as alarms, with a repeatable set of inputs. Preferably there is an automatic alarm test which will cause the arrythmia monitoring computer to generate almost its entire repetoire of alarms messages during a single one hour test. Another preferable automatic test is a paced rhythm test which will generate most of the alarms associated with paced rhythm. (A paced rhythm is a rhythm created by a heart stimulated by a pacemaker.) A further automatic test is a ventrical premature beat (VPR) step test which generates a stairstep trend plot that can quickly verify calibration of an arrhythmia system equipped with a VPB trend plotter. Such a plotter graphically indicates the number of abnormal beats per minute a patient has had over a designated period of time.

The "200/HG" key is used by the operator to set the pressure waveform generated by this device at a calibration level. The calibration level is determined by the input exitation amplitude. All subsequently selected levels will be linearly proportional to this initial level. The "sys" and "dias" keys are used by the operator to set the systolic and diastolic levels respectively, of the simulated pressure waveform. After either key is actuated, the "select number" indicator is lighted which tells the operator to enter a number representing the level being set.

The "resp" key is used by the operator to set the respiration rate of the simulated patient. After it is actuated, the "select number" indicator is lighted and the operator then enters a number representing the selected respiration rate.

Figure 2:
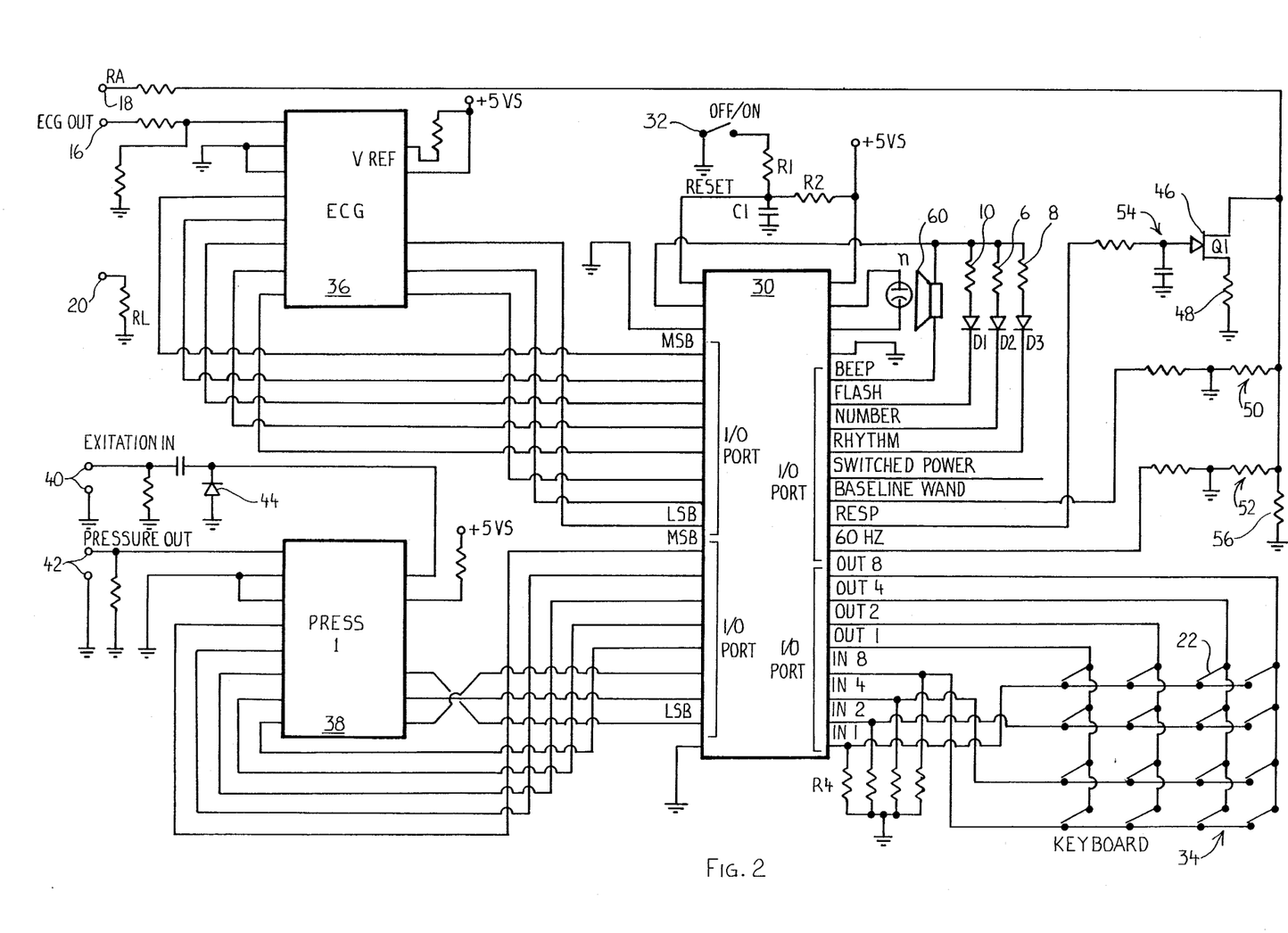
FIG. 2 is a schematic representation of the main functional parts of the invention.

The description will now focus on the hardware of the device. Referring to FIG. 2, a schematic representation of the electronic circuits is shown. The control means of the device is a central processing unit 30 which is adapted to be responsive to a control program. The control program resides in a program memory which is preferably integral with the central processing unit (CPU). The program memory is accessible for at least reading by the CPU. Accessable to the CPU for writing as well as reading is a data memory primarily for storing variables such as changeable parameters and calculation variables. Preferably the data memory is integral with the CPU and the program memory.

In the preferred embodiment, the CPU and both memories are embodied in an 8-bit microcomputer unit such as the Motorola MC1468705G2 which is a complimentary metal oxide semiconductor (CMOS) integrated circuit containing CPU circuits, random access memory (RAM), and eraseable/programmable read-only-memory (EPROM), bootstrap read-only-memory and other functions. The microcomputer unit (MCU) is preferably powered by generally 5 volts to which is connected a power on reset circuit comprising an on/off switch 32, a pair of resistors, R1 and R2 in divider configuration, and a capacitor C1. When power is applied, the switch 32 is opened permitting C1 to charge through R2. The time constant of the C1 and R2 network is long enough to provide a suitable reset to the MCU.

The MCU has a plurality of input/output ports adapted to provide a communication path between the CPU and devices external to the CPU. In the MCU, these input/output (I/O) ports comprise four 8 bit, bi-directional ports. Preferably, 4 bits of one port are used to send signals to a 4×4 key pad switch matrix 34, and the other 4 lines of the I/O port are used for receiving signals from the key pad matrix. The lines designated "in 1", "in 2", "in 4", and "in 8" are strobed one at a time with a voltage and the lines designated "out 1" through "out 5" are each read by the MCU to detect the presence of a closed key pad switch. The actuation of each key pad is detected by the coincidence of a strobed voltage on an output line and the presence of a voltage on an input line. Electrically connected to each output line is single pull-down resistor R4 for termination purposes.

A second of the I/O ports of the MCU is used to output data groups, preterably 8-bit bytes, to a first digital to analog conversion means (DAC) 36. The DAC is adapted to convert each byte from the second I/O port to an analog signal, the amplitude of which corresponds to the amplitude represented by the byte. The output of the DAC is labeled "LA" and is the signal transmitted to an arrhythmia monitoring system via the "LA" post 16. The "RL" post 20 is seen to be connected to device ground.

The RA circuit consists of attenuators, integrators, and a summing injunction which combines the logic levels present at the 60 Hz and Baseline Wander outputs of the MCU and conditions them to a level suitable for connection to an EKG machine (electrocardiograph).

In addition to the entire network presents a dynamic impedance similar to that of a breathing patient via a JFET connected to the RESP output port of the MCU. The shunt resistance caused by the JFET can be applied to the LA or RA connectors via a switch. This dynamic impedance is preferably 2000 ohms with a 0.5 ohm periodic variability.

To a device interfacing with the inputs of an EKG machine, the EKG machine looks like a differential amplifier. The LA is the + input, RA is the − input, and RL is connected to ground.

A third I/O port of the MCU communicates in likewise fashion to a second DAC 38. This DAC provides analog signals which represent the pressure of the simulated patient. This is communicated to the arrhythymia monitoring system via the pressure out jack (not shown). There is also a fifth jack (not shown) by which the second DAC receives excitation voltage. The excitation voltage is supplied by the patient pressure monitor and is typically ac at a frequency of 2.4 KHz.

As previously discussed, a control program resides in the program memory in the MCU. It is programmed, designed and adapted to, in response to operator inputs, cause the central processing unit to output, via the second I/O port, a periodic string of bytes, each byte representing an amplitude at some point in time of an EKG waveform.

The description will now focus on the software and memory utilization of the device.

A Period look-up table (LUT) is used to convert a binary number representing a heartbeat rate into a binary number representing the period of the heartbeat rate. The heartbeat rate is stored in a Last Rate memory location. The period LUT is indexed by Last Rate, that is, the contents of Last Rate are used to address the Period LUT when fetching data. The data fetched from the table represents the heartbeat period and is compared with a Period Clock to determine if a heartbeat period has elapsed. If so, a Period Done flag is set.

An Arrhythymia Time Delay LUT converts a binary number representing the number of occurrences of a secondary rhythm per minute into a binary number representing a time delay. The number of occurrences per minute is stored in the Last Number of Arrhythymias memory location. The LUT is indexed by the Last Number of Arrhythmyias at suitable times when the chosen arrhythymia pattern is v/min or run/v. The data fetched is the time delay. After the data is fetched, it is compared with the contents of an Arrhythmyia Clock which measures the time from a last preceding secondary rhythm. When the time delay matches the count in the Arrhythmyia Clock, an Arrhythmyia Ready flag is set and the Arrhythmyhia Clock is cleared to zero. This causes an Active Rhythm memory location to be loaded from a Last Arrhythmyia memory location rather than from a Last Rhythm memory location when the previous waveform is done and a heartbeat period has elapsed.

A Respiration LUT converts a binary number in a Respiration Rate memory location into a binary value representing time between settings of bit 1 of I/O port D. The number in Respiration Rate represents the respiration rate of the simulated patient. Bit 1 of port D being set gates on a JFET which, in turn, lowers the output impedance of post "RA". A conventional respiration monitor (which this device is adapted to test) would interpret the change in output impedance as a change in conductivity between the "RA" electrode (affixed by conductive paste to a patient's right arm) and the "RL" electrode (affixed by conductive paste to the patient's right leg). Such a change would occur in a real patient when the patient's chest contracts while exhaling. When bit 1 of port D is cleared, the JFET is shut-off and the "RA" output increases in impedance as when a patient inhales.

A Pressure LUT contains a plurality of digitized incremental samples of a pressure waveform. It is indexed by the contents of a Pressure Library Pointer memory location. The Pressure Library Pointer initially gets loaded with a calculated pressure starting point when a Pressure Sync flag is set. During each hardware timer interrupt, an incremental sample is fetched from the LUT and is algebraically added to the contents of an I/O port A which is the digital input to a pressure DAC, and the Pressure Library Pointer gets incremented. The DAC converts the data stream from port A into an analog representation of a pressure waveform. If a Low Pressure flag is set, the sample fetched is suitably reduced prior to the addition. If the reduced or unreduced sample is less than a calculated diastolic, then the calculated diastolic is output to port A, and Pressure Library Pointer is not incremented and remains static until it is again loaded with the calculated pressure starting point due to a true condition of the Pressure Sync flag.

An EKG LUT contains a plurality of digitized EKG rhythms. The LUT is indexed by the contents of an EKG Library Pointer memory location which gets loaded initially from an Active Rhythm memory location. During each hardware timer interrupt, a sample of a rhythm, primary or secondary, is fetched from the LUT and output to an I/O port B which is the digital input to an EKG DAC, and EKG Library Pointer is incremented. The DAC converts the data stream from port B into an analog representation of an EKG rhythm. Within the EKG LUT samples are embedded codes representing pressure synchronization, low pressure, and end-of-waveform conditions. If the sample fetched contains a code representing a pressure syncronization or low pressure condition, then the Pressure Sync flag or the Low Pressure flag, respectively, is set. If it is a code signifying an end of the current active rhythm, then an End-of-Waveform flag is set.

The primary timer is a hardware timer which causes an interrupt, that is, a hardware timer interrupt (HTI), every 2 msec.. The HTI is used to update all other counters and clocks, and to update the EKG and pressure waveform samples.

Ripple Count is a one byte memory location where a "ripple" count is kept. Ripple Count is incremented every 2 msec. during the HTI. It is used for several purposes. Bit 0, the least significant bit of the ripple count, is used in conjunction with the Peds modifier to increase the high frequency components of a rhythm. The condition of the Peds modifier being true and bit 0 being true causes EKG Library Pointer to be incremented twice during a single HTI. This causes two samples of the active rhythm to be skipped, which has the effect of shortening in time the active rhythm and causing sharper changes in the rhythm to more closely simulate a child patient. Bit 3 of the ripple count is used in conjunction with the 60 hz modifier to inject 60 hz noise into the outputs of this invention. If the active rhythm has an irregular period, the contents of Ripple Count are used to quasi-randomly modify the contents of Period Clock.

A Minute Clock is a two byte memory location where a minute is counted. It is incremented every 2 msec. by HTI and tested after incrementing to see if one minute has elapsed. If so, the minute clock is cleared to 0 and a Run Time Minute Timer is incremented. The Minute Clock is also cleared immediately after a binary encoded key entry is loaded into the Last Number of Arrhythmias whenever a v/min or run/v pattern of arrhythmia is selected.

A Period Clock is a 2 byte memory location where the period of a heartbeat is counted. It is incremented every 2 msec. during HTI, and tested after incrementing to see if its contents equal a time value fetched from a Period LUT, using Last Rate as an index, which represents the period of the primary rhythm. It is cleared if Last Arrhythmia contains a number representing an arrhythmia which will cause a premature beat. Period Clock is modified if the active rhythm will cause a premature beat or if the active rhythm has an irregular period.

An Arrhythmia Clock is a 2 byte memory location in which the time between secondary rhythms is counted. It is incremented every 2 msec. by HTI. It is also tested during HTI to see if it contains a value equal to a timed delay value fetched from an Arrhythmia Time Delay LUT. It is also cleared immediately after Last Number of Arrhythmias is loaded from key entries after v/min or run/v are selected.

An Arrhythmia Scratch Count is a 1 byte memory location which contains a scratch count used in the production of arrhythmias. If the selected arrhythmia is a bigem, trigem or run/v the scratch count gets incremented each time a secondary rhythm is produced. When the bigem modifier is set, bit 0 of the scratch count acts as a divide by two counter, and ensures that a secondary rhythm follows each primary rhythm. When the trigem modifier is set, bits 0 and 1 of the scratch count are operated as a divide by 3 counter, and ensure that a secondary rhythm will occur after each pair of primary rhythms. When the run/v modifier is set, the scratch count is used to count the number of consecutively occurring secondary rhythms. When the scratch count equals the contents of Last Number of Arrhythmyias, the current run of arrythymias is ceased and Arrhythmyia Scratch Count is cleared to zero. The scratch count is also cleared immediately after Last Number of Arrhythmias is loaded from key entries after v/min or run/v is selected.

A Run Time Minute Timer is a 1 byte memory location which is incremented by the Minute Clock, that is, it contains a count of the minutes which have elapsed during a given run of an EKG waveform. It is cleared whenever a new key is pushed. When waveforms are being recalled from user memory, it is cleared whenever a new waveform is recalled. It is also used to determine the automatic shut-off time. When the timer reaches 240, the device shuts down as if the off switch was hit.

A Respiration Clock is a 2 byte memory location which is incremented every 2 msec. by HTI. It is then compared with a value fetched from a LUT using Respiration Rate as an index. If there is a match, then bit 1 of port D is set and the Resp Clock is cleared. It is cleared when bit "0" of the respiration clock Hi byte is set, then bit 1 of port D is cleared.

Wave Done is a flag which indicates that production of the current rhythm is completed. It is set during an HTI when the value fetched from the EKG LUT is a code indicating that the end of the thythm has been reached. It gets cleared by the power-on routine.

Period Done is a flag which indicates that the current period is finished. (The time period of each rhythm, both primary and secondary, is determined by the value stored in the device memory location Last Rate, except in certain situations where the time period is altered by the program.) It gets set during an HTI when the period clock equals a value fetched from a period LUT using Last Rate as an index, or it gets set during an HTI when certain selected arrhythmyias would naturally cause a premature termination of the rhythm being currently produced. Both Wave Done and Period Done get cleared whenever device memory location Active Rhythm gets loaded.

Arrhythmyia Ready is a flag which indicates that the time is right for the production of a v/min or run/v secondary rhythm. It gets set during an HTI if the Arrhythmyia Clock equals a time value fetched from the Arrhythmyia Time Delay LUT indexed by either Last Number of Arrhythmyias (if the v/min flag is set) or a constant (if the run/v flag is set). In other words, it gets set if enough time has elapsed since production of the last secondary rhythm. It gets cleared during an HTI whenever the device initiates production of a bigem, trigem, or v/min secondary rhythm; and it gets cleared whenever the device initiates the production of the last secondary rhythm in a run of run/v secondary rhythms. Note that it is only used by the v/min and run/v routines to indicate that the Arrhythmyia Clock has counted out the proper time delay from a last preceding arrhythmyia.

A rhythm is produced by a series of samples output to a DAC. The samples are 2 msecs, apart in time, and one sample is output per each HTI. Each sample is fetched from an EKG LUT using memory location Active Rhythm as the primary pointer to the proper set of samples in the EKG LUT. In other words, at the start of a rhythm production, the contents of Active Rhythm determines which rhythm will be produced.

Active Rhythm is initially loaded during a power-on routine to produce a normal sinus rhythm. Thereafter it is loaded from memory location Last Rhythm or memory location Last Arrhythmyia depending on the condition of certain flags and counters.

If an arrhythmyia flag is set, Active Rhythm will be loaded from either Last Rhythm or Last Arrhythmyia depending on the condition of other flags and counters. If the period of the previous rhythm is done and the bigem flag is set, the loading of Active Rhythm will be determined by the state of bit 0 of Arrhythmyia Scratch Count. If the period of the previous rhythm is done and the trigem flag is set, the loading of Active Rhythm is determined by bit 1 of Arrhythmyia Scratch Count. If the period of the previous rhythm is done and the v/min flag is set, the loading of Active Rhythm is determined by the state of the Arrhythmyia Ready flag. If the period of the previous rhythm is done and the run/v flag is set, the loading of Active Rhythm is determined by the state of the Arrhythmyia Ready flag. If the period of the previous rhythm is lone and no arrhythmyia flags are set, Active Rhythm gets loaded from Last Rhythm.

I claim:

1. A method of generating a simulated continuous heartbeat comprising the steps:
   (a) selecting a rhythm by an operator input means,
   (b) selecting a heartbeat rate by an operator input means,
   (c) converting the selected heartbeat rate to an impulse period by means of a period look-up table, the selected heartbeat rate being used to index the look-up table,
   (d) using the selected rhythm as a guide to a first sample, retrieving in sequential order and generally at uniform time intervals a set of individual digitized samples of the selected rhythm from a memory, the set comprising enough samples to reproduce the rhythm,
   (e) converting each individual digitized sample to an analog signal by means of a digital to analog converter,
   (f) processing the analog signal to remove unwanted high frequency components by means of a signal filter,
   (g) after the last sample has been converted, causing the processed analog signal to become steady state,
   (h) measuring time from the conversion of the first digitized sample,
   (i) comparing the impulse period with measured time until a match occurs, and
   (j) repeating steps (d) through (i).

2. A method of generating a simulated continuous heartbeat with an arrhythmia, comprising the steps:
   (a) loading indexing information corresponding to a selected primary rhythm into a memory means adapted to be an index means to a rhythm look-up table containing a plurality of sets of individual digitized samples, each set comprising in sequential order all of the samples necessary to produce one and only one of a plurality of unique rhythms,
   (b) using the indexing means to retrieve in sequential order and generally at uniform time intervals a set of individual digitized samples from the rhythm look-up table, the set uniquely corresponding to the indexing information,
   (c) converting each individual digitized sample to an analog signal by means of a digital to analog converter,
   (d) processing the analog signal to remove unwanted high frequency components by means of a signal filter,
   (e) after the last sample has been converted, causing the processed analog signal to become steady state,
   (f) measuring time from the conversion of the first digitized sample,
   (g) comparing the measured time with an impulse period derived from a selected heartbeat rate by means of a period look-up table until a match occurs,
   (h) determining if the next rhythm produced should be a selected secondary rhythm,
   (i) if not, then loading the indexing information corresponding to the selected primary rhythm into the indexing means, but if so, then loading indexing information corresponding to the selected secondary rhythm into the indexing means, and
   (j) repeating steps (b) through (i).

3. The method of claim 2 wherein step (h) comprises the step of determining if the last rhythm produced was the primary rhythm.

4. The method of claim 2 wherein step (h) comprises the step of determining if the last two rhythms produced included a primary rhythm.

5. The method of claim 2 wherein step (h) comprises the steps:
   (h-1) measuring time from the last production of the secondary rhythm or, if no secondary rhythm has been yet produced, from a suitable start-up point, and
   (h-2) comparing the time measured from the last secondary rhythm or from the suitable start-up point with a time delay derived from a preselected number to determine if the elapsed time is equal to or greater than the time delay.

6. The method of claim 2 wherein steps (h) and (i) comprises:
   (h-1) measuring time from production of the first secondary rhythm of a last run of secondary rhythms or, if no run has yet occurred, then from a suitable start-up point,
   (h-2) comparing the time measured with a present time delay value to determine if the elapsed time is equal to or greater than the time delay,
   (h-3) if so, then setting a flag means to remember that a run is underway,
   (h-4) counting each secondary rhythm produced in a run,
   (h-5) comparing the count with a preselected number,
   (h-6) if the count equals the number, then clearing the flag means, and
   (i) if the flag means is set then loading the secondary rhythm identifying information into the EKG indexing means, but if the flag is cleared, then loading the primary rhythm identifying information into the EKG indexing means.

7. The method claim 1 or 2 further comprising the steps:
   (a) loading a value derived from preselected blood pressure systolic and diastolic levels into a memory means adapted to be an index means to a pressure lock-up table containing a set of individual digitized increments of a blood pressure waveform,
   (b) using the pressure indexing means to retrieve in sequential order and generally at uniform time intervals the set of increment samples,
   (c) algebraically adding each increment to an accumulator,
   (d) converting the output of the accumulator to an analog signal,
   (e) comparing the output of the accumulator each time an addition takes place to determine if the output is a value less than a number derived from the preselected diastolic level,
   (f) if so, then loading the accumulator with the number derived from the preselected diastolic level, and repeating steps (a) through (f), and
   (g) if not, then incrementing the pressure index means, and repeating steps (b) through (g).

8. The method of claim 1 or 2 further comprising the steps of:
   (a) continuously measuring time by regularly incrementing a counter means, (b) after each increment, comparing the time measured with a time value derived from a preselected respiration rate, and (c) when a match occurs, suitably altering the impedance of an output terminal simulate the respiration of a patient.

9. The method of claim 1 or 2 wherein the time interval generally separating the retrieval of each contiguous pair of digitized rhythm samples is varied to add high frequency components to the rhythm to more closely simulate the heartbeat of an infant and a small child.

10. The method of claim 1 or 2 wherein the steady state signal is mixed with a time varying signal to simulate electrical ground noise and/or patient movement.

11. The method of claim 1, 2, 5 or 6 further comprising the step of continuously marking time at a regular interval, the uniform time interval generally separating the retrieval of each contiguous pair of digitized rhythm samples being equal to the interval between two successive marks, all times being measured by counting the marks.

12. The method of claim 2 wherein the preselection are codes derived from operator inputs, which derived codes are stored in a short-term memory means for use in the immediate production of a simulated heartbeat.

13. The method of claim 2 wherein the preselections are codes which are recalled as a set from a preprogrammed long-term memory means capable of storing a plurality of such sets, which recalled codes are stored in a short-term memory means for use in the immediate production of a simulated heartbeat.

14. A device for generating a simulated continuous heartbeat comprising:

(a) a means for operator inputing information identifying one of a plurality of unique heartbeat rhythms, (b) a means for operator inputing information identifying a desired hearbeat rate, (c) a first means for storing the rhythm identifying information, (d) a second means for storing the rate identifying information, (e) a means for converting the heartbeat rate identifying information into a period of the heartbeat rate, (f) a means for measuring elapsed time, (g) a means for comparing the heartbeat period with the elapsed time and for resetting the time measuring means when a match occurs, (h) a means for setting a first flag signifying that a time equal to the heartbeat period has elapsed when said match occurs, (i) a third means for storing a plurality of sets of digitized samples of rhythm patterns, each set comprising in sequential order all the samples required to produce one and only one of the plurality of selectable rhythms, (j) a means for retrieving sequentially from the third storing means all of the samples associated with the rhythm identified in the first memory means, (k) a means for sequentially receiving the digitized samples from the third storing means and converting them to corresponding analog signals, (l) a means for synchronously starting the elapsed time measuring means and the sample retrieving means, and for timing the retrieving of samples from the third storing means and the transferring of said samples to the conversion means such that all necessary samples of the selected rhythm get uniformly transferred to the conversion means within a time less than or equal to the heartbeat period, (m) a means for setting a second flag when all necessary samples of a set have been transferred to the conversion means, (n) a means for recognizing the second flag and in response thereto suspending the conversion means until the first flag is set suspension of the conversion means causing the conversion means to produce a constant reference signal, and for then clearing both flag means, and further for resetting and restarting the synchronous starting and timing means whenever the flags are cleared, and (o) a means for filtering the signals from the conversion means to produce a generally continuous processed heartbeat having the desired heartbeat rate.

* * * * *

UNITED STATES PATENT AND TRADEMARK OFFICE
CERTIFICATE OF CORRECTION

PATENT NO. : 4,736,322
DATED : April 5, 1988
INVENTOR(S) : Ralph D. Clifford

It is certified that error appears in the above-identified patent and that said Letters Patent is hereby corrected as shown below:

Column 12, claim 6, line 26 "present" should be --preset--

Column 12, claim 7, line 46 "lock-up" should be --look up--

Signed and Sealed this

Fourth Day of October, 1988

Attest:

DONALD J. QUIGG

*Attesting Officer*  *Commissioner of Patents and Trademarks*